(12) United States Patent
Ohara et al.

(10) Patent No.: US 6,394,650 B1
(45) Date of Patent: May 28, 2002

(54) PHOTOGRAPHIC COMBINATION FOR USE IN RADIOGRAPHY

(75) Inventors: Hiromu Ohara; Chika Honda; Akira Ishisaka, all of Tokyo (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/694,743

(22) Filed: Oct. 23, 2000

(30) Foreign Application Priority Data

Oct. 27, 1999 (JP) .............................................. 11-305713

(51) Int. Cl.$^7$ .............................................. G03B 43/02

(52) U.S. Cl. ....................................... 378/182; 378/185

(58) Field of Search .................................. 378/182, 185

(56) References Cited

U.S. PATENT DOCUMENTS

| | | | | |
|---|---|---|---|---|
| 5,070,248 A | * | 12/1991 | Pesce | 250/483.1 |
| 5,461,660 A | * | 10/1995 | Dooms et al. | 378/185 |
| 5,684,851 A | * | 11/1997 | Kurbatov et al. | 378/87 |

* cited by examiner

Primary Examiner—Robert H. Kim
Assistant Examiner—Allen C. Ho
(74) Attorney, Agent, or Firm—Frishauf, Holtz, Goodman, Langer & Chick, P.C.

(57) ABSTRACT

A photographic combination for use in radiography to project a refraction contrast image is disclosed, comprising a radiographic intensifying screen and a silver halide light sensitive photographic material, wherein the photographic material comprises a support having on only one side of the support a light sensitive layer, the photographic combination exhibiting a speed of 200 to 750. A radiographic system comprising an X ray source and the photographic combination is also disclosed.

16 Claims, 2 Drawing Sheets

PHOTOGRAPHIC COMBINATION FOR USE IN RADIOGRAPHY

FIELD OF THE INVENTION

The present invention relates to a high speed photographic combination for radiographic use and radiography by use thereof, and in particular to a photographic combination for radiographic use, exhibiting high sensitivity and superior image quality, suitable for high quality mammography, and radiography by the use thereof.

BACKGROUND OF THE INVENTION

For diagnosis of breast cancer, specifically diagnosis of breast cancer at the initial stage, for example, is useful a photographic combination for mammographic use which is comprised of a radiographic intensifying screen and a silver halide photographic material (hereinafter, also referred to as a screen film system), whereby micro-calcification having a size of some hundreds micrometers or less can be detected at the initial stage of cancer. Specifically, relatively low speed photographic materials exhibiting superior graininess are employed in the conventional photographic combination for mammographic use.

To enhance the detectability thereof, further enhanced sharpness in the screen film system has been desired. For example, a radiographic combination of a silver halide photographic material having a silver halide emulsion layer coated on only one side of a support (a so-called single-sided coated film) and a fluorescent screen (or X-ray intensifying screen) in the back screen arrangement is employed to achieve enhanced sharpness. Further, increasing the contrast of the single-sided coated film or prolonging the developing time in processing is conducted to achieve a contrast-increase in the film.

SUMMARY OF THE INVENTION

Although sharpness can be enhanced by a contrast-increase of the film, however, there occurs a self-inconsistency such that the contrast-increase results in deteriorated graininess. For example, not only observation of micro-calcification but also detection of a low contrast image of a tumor having a size of about 1 cm is dispensable in diagnosis of breast cancer. Accordingly, enhancement of sharpness without causing deterioration in graininess is desired in mammography.

Deterioration of graininess caused by a contrast-increase of the film can be improved by increasing the X-ray dose, which must be limited in terms of patient exposure to radiation. Further, an x ray source of molybdenum is often employed for mammography since the use of an X ray source giving high exposure to radiation is not suited. Furthermore, there have been made attempts of enhancing graininess of a silver halide photographic material but the size of silver halide grains used in the silver halide photographic material used for mammography is so small that this technique is close to its limitation.

To enhance detectability, micro-calcification images can be can be detected to further smaller levels by applying magnification radiography. This technique is employed in mammography. However, magnification radiography results in blurring of images due to geometrical unsharpness in the detection of tumor. This blurring is unsharpness due to so-called penumbra, depending on the focus size of X ray tube (3) and the magnification factor, shown as blur 5 in FIG. 1. In the mammography used in the field of the medical diagnosis, it was difficult to enhance detectability of both micro-calcification and tumor, with maintaining the patient exposure to radiation at a low level.

It was found by the inventors that this blurring can be overcome by applying a refraction or phase contrast imaging technique. In cases when this technique is allied to mammography, the distance of from X ray tube 3 to photographic combination 2 needs to be increased. In such a case, the use of a high speed photographic combination was found to be effective to overcome the foregoing problems. The combination of the high speed photographic combination with the refraction contrast imaging technique enhances the boundary (or edge) image of the object to be detected, leading to prevention of blurring. In this case, a sharp boundary image was obtained by the use of the high speed photographic combination, without increasing the X-ray dose to the photographic combination. It was further proved that the high speed photographic combination was effective for an enlarged image of fine mineral that was projected onto the photographic combination, even when the intensity of a X ray source was low. Thus, it was found that the use of the high speed photographic combination in the refraction contrast photographing enhances detectability of fine mineral images as well as detectability of tumor, while maintaining the low exposure exposure to radiation.

In view of the foregoing, it is an object of the present invention to provide a photographic combination for radiographic use, exhibiting high sensitivity and superior image quality, suitable for high quality mammography, and radiography by the use thereof.

The above object of the invention can be accomplished by the following constitution:

1. A radiographing system comprising a X ray source and a photographic combination onto which an image of X rays emitted from the X ray source and passing through an object is projected and which comprises a radiographic intensifying screen and a silver halide light sensitive photographic material comprising a support having on only one side of the support a light sensitive layer, wherein the X ray image is one which has been edge-enhanced through refraction contrast enhancement and enlarged, the photographic combination exhibiting a speed of 200 to 750;
2. The radiographic system described above 1, wherein the radiographic system is a mammographic system.
3. The radiographic system described in above 2, wherein the object is a breast;
4. The radiographic system described above 2, wherein the X ray source is a molybdenum tube;
5. The radiographic system described in bove 1, wherein a distance between the X ray source and the object is not less than 50 cm, a distance between the X ray source and the photographic combination being not less than 75 cm;
6. The radiographic system described in above 5, wherein the X ray source is a molybdenum tube;
7. The radiographic system described in above 1, wherein the radiographic intensifying screen exhibits a sensitivity of 200 to 500;
8. The radiographic system described in above 1, wherein the speed of the photographic combination is a system speed based on a photographic speed of the light sensitive layer and a sensitivity of the radiographic intensifying screen;
9. A photographic combination for use in radiography to project a refraction contrast image comprising a radiographic intensifying screen and a silver halide light sensitive photographic material, wherein the photographic material comprises a support having on only one side of the support a light sensitive layer, the photographic combination exhibiting a speed of 200 to 750;

10. The photographic combination of claim 9, wherein the photographic combination is used for mammography;

11. The photographic combination described in above 9, wherein the screen exhibits a sensitivity of 200 to 500;

12. The photographic combination described in above 11, wherein the radiographic intensifying screen exhibits a contrast transfer function of 0.5 to 1.0 at a spatial frequency of 2 line/mm;

13. The photographic combination described in above 9, wherein the radiographic intensifying screen comprises a binder containing a hydrophilic group;

14. The photographic combination described in bove 9, wherein the photographic material exhibits a sensitivity of 1.0 to 3.0 and an average contrast of 2.5 to 4.5;

15. A radiographing method, wherein an refraction contrast radiographic image is photographed using a photographic combination as claimed in claim 9 and wherein an X ray source, an object and the photographic combination are arranged in this order so that the distance between the X ray source and the object is not less than 50 cm and the distance between the object and the photographic combination is not more than 75 cm; and 16. The radiographic method described in above 15, wherein the X ray source is a molybdenum tube.

EMBODIMENTS OF THE INVENTION

Figure 1:
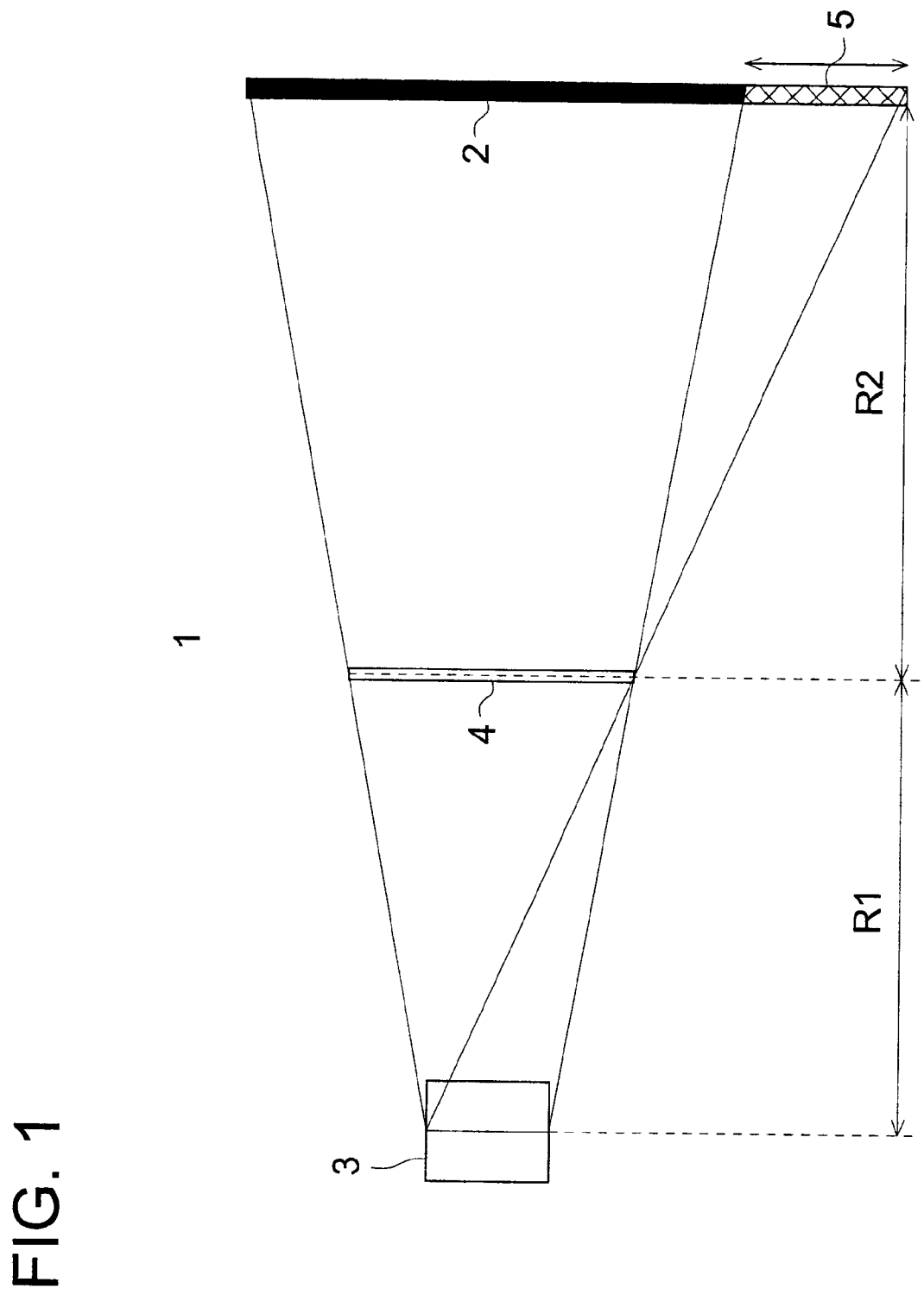
FIG. 1 illustrates a schematic radiographing apparatus and blurring occurred therein.
Figure 2:
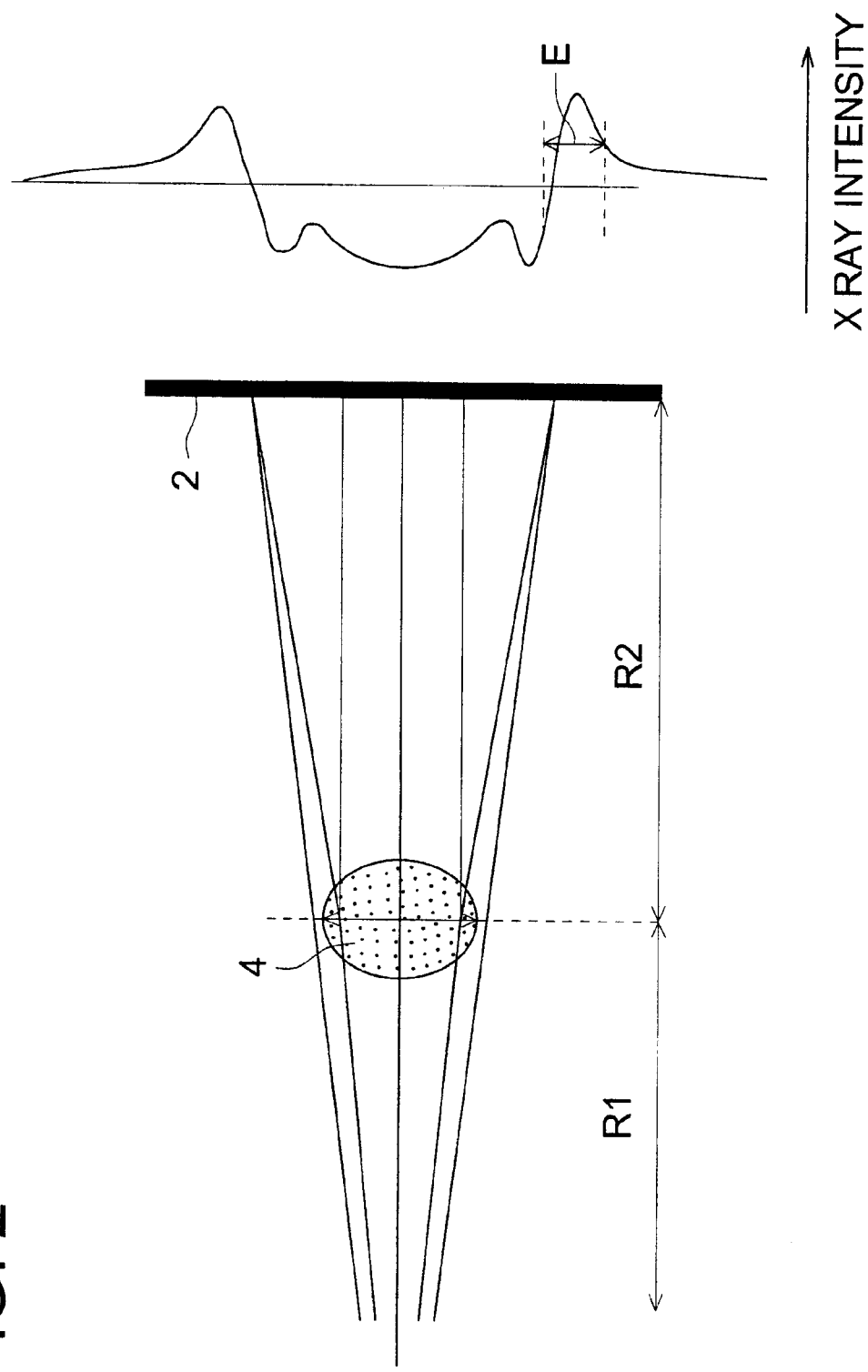
FIG. 2 illustrates a schematic radiographing apparatus and edge enhancement in radiography.

The photographic combination for radiographic use according to this invention and the radiography by the use thereof will now be described further in detail, based on the drawings but the present invention is not limited to the description of these embodiments or the drawings. FIG. 1 illustrates blurring in magnification radiography and FIG. 2 illustrates edge enhancement in radiography.

An X ray photographing apparatus (1) used in this invention is provided with the photographic combination (2) of a radiographic intensifying screen and a silver halide photographic material which is single coated, that is, coated with a light sensitive layer on only one side of the support and an X ray tube (3), whereby X ray refraction contrast images are photographed, in which R1 is the distance between the x ray tube (3) and an object (4), and R2 is a distance between the object (4) and the photographic combination (2).

To enhance detectability in X ray imaging, besides contrast-increasing of the silver halide photographic material of the photographic combination (2), micro-calcification images can be detected to further smaller size levels by applying magnification radiography. In this method the same effect as an enhancement of sharpness can be achieved without deteriorating graininess and a magnifier is usually employed in viewing of mammography.

However, magnification radiography results in blurring of images due to geometrical unsharpness. This blurring is unsharpness due to so-called penumbra, depending on the focus size of X ray tube (3) and the magnification factor, as shown in FIG. 1, blurring 5. This blurring can be overcome by the refraction contrast imaging technology in this invention. In cases when this imaging technology is applied to mammography, the distance between the X ray tube (3) and the photographic combination (2) needs to be increased, so that a photographic combination exhibiting high image quality and high sensitivity is needed to overcome the foregoing problem. Thus, enhancement of detectability of micro-calcification without deteriorating detectability of the tumor can be achieved by application of magnification radiography with a high speed photographic combination (2), without deteriorating the image quality.

Accordingly, it is an object of this invention to provide a high speed photographic combination for use in radiography to conduct magnification radiography of enhanced image quality and an X ray imaging method by the use of the same, as specifically described in detail below.

X rays are electromagnetic waves, having properties of wave. When an X ray beam penetrates objects differing in their refractive index, refraction occurs at the interface thereof.

As is schematically shown in FIG. 2, in the X ray transmission image (E) at the interface differing in their refractive index between the front and rear, a portion in which the X ray density is decreased by refraction of the X ray and a portion in which the X ray density is increased by overlapping of a refracted X ray beam with a rectilinear X ray beam are produced, resulting in an edge-enhanced image. Such a phenomenon is called a refraction contrast. Conventional X ray images exhibit only an absorption contrast based on a difference in absorption and such a refraction contrast has not been fully employed so far.

In the invention, even when blurring of an image is caused by penumbra in magnification radiography, such blurring can be overcome by applying the refraction contrast to cause edge enhancement, leading to a magnified X ray image exhibiting superior sharpness. Thus, a photographic combination comprised of a radiographic intensifying screen and a silver halide photographic material having a light sensitive layer on one side of the support, i.e., a screen-film system is employed in X ray imaging, in which the intensifying screen is exposed to X ray and emits visible light in response to the X ray dose, after which the silver halide photographic material is exposed the emitted light. Therefore, sensitivity of the photographic combination (2) depends on the combination of the intensifying screen with the silver halide photographic material used therein. In conventional enlarging mammography, a distance (R1) between X ray tube (3) and object (4) is variable from 30 to 50 cm, and a distance (R2) between the object (4) and photographic combination (2) as an X ray detector is variable to 30 to 10 cm, therefore, the distance between the X ray tube (3) and the photographic combination (2) is at most 60 cm. The exposure dose at this distance is 5 to 10 mR and the conventional screen-film for use in mammography is constituted so as to meet such exposure conditions.

As an X ray tube (3) of an X ray source used in mammography is usually employed a molybdenum tube, the focus size of which is usually a small focus, e.g., 100 μm. In this case, it was further proved that the distance of from the x ray source to the object needed to be at least 50 cm to obtain satisfactory refraction contrast images. Furthermore, the distance of from the object (4) to the photographic combination (2), that is, a screen-film system needs at least 25 cm. Thus, the distance of the X ray tube (3) to the screen-film system of the photographic combination (2) needs at least 75 cm to obtain a refraction contrast image employing a 100 μm molybdenum tube, in which the exposure dose is not more than 4 mR.

Such a dose is too low in sensitivity for a commonly known screen-film system of a photographic combination (2) for use in mammography, so that a screen-film system capable of photographing at such a dose is required.

The present invention accomplished by providing a photographic combination of a radiographic intensifying screen with a silver halide photographic material which is coated with a light sensitive layer on only one side of the support, characterized that the photographic combination exhibits a photographic speed of 200 to 750, and preferably 200 to 500.

The speed of combination (2) of a radiographic intensifying screen with a silver halide photographic material which is coated with a light sensitive layer on only one side of the support is determined according to the following procedure. Using X rays generated in a molybdenum target tube operated at a three phase electric power source of 28 kVp and transmitted through a 1 mm beryllium filter, a 0.03 mm molybdenum filter and 2 cm acryl filter, the photographic combination (2) is subjected to exposure and the silver halide photographic material is subjected to photographic processing at 34° C. for 90 sec. using automatic processor SRX-502 (available from Konica Corp.) with developer XD-SR and fixer XF-SR (both, available from Konica Corp.). Herein, the speed of the photographic combination is represented by a relative value of the reciprocal of an X ray exposure amount necessary to give a density of 1.0 plus a fog density, based on the speed of the combination of intensifying screen MD100 and silver halide photographic material CMH being 100.

The photographic combination for use in mammography, as used in this invention needs higher sensitivity, while screen film systems in general result in deteriorated sharpness or graininess when sensitivity of the system is enhanced.

Provided in the present invention is a photographic combination (2) for use in mammography exhibiting enhanced sensitivity and superior sharpness. Thus, one preferred embodiment of this invention is the photographic combination for use in radiography, characterized in that a radiographic intensifying screen exhibits a sensitivity of 200 to 500 and a contrast transfer function of 0.5 to 1.0 at a spatial frequency of 2 lines/mm.

The sensitivity of a radiographic intensifying screen can be measured in the following manner. An X ray film for use in mammography, CMH available from Konica Corp. is employed, which is combined with intensifying screen MD 100, available from Konica Corp. to form a photographic combination. A molybdenum target X ray tube, a 1 mm thick beryllium filter, a 0.03 mm thick molybdenum filter and a 2 cm thick acryl filter were used, at a position of 60 cm apart from which the screen-film combination is placed and exposed to x ray from the film side. The exposure amount of X ray is adjusted by varying the mAs value of the X ray tube. After processing, the reciprocal of the X ray exposure amount necessary to give a density of 1.0 plus a fog density is determined, which is defined as the sensitivity of this combination comprised of an intensifying screen and a silver halide photographic material being 100. The relative sensitivity of an intensifying screen is determined similarly to the above, provided that screen MD100 is replaced by the screen to be measured, which is combined with film CMH. The processing is carried out at 34° C. for a period of 90 sec., using automatic processor SRX-502, developer XD-SR and fixer XF-SR (each of which is available from Konica).

The contrast transfer function (CTF) refers to a physical value representing a sharpness of an image obtained in the combination used therein. The maximum value is 1.0, the minimum is 0.0, of which the larger value is the superior sharpness. The measurement thereof is made as follows. A rectangular lead or tin chart is allowed to be in close contact with the photographic combination and exposed to X ray. The rectangular images obtained after processing are subjected to densitometry using a microdensitometer and thereby a contrast transfer function (CTF) is obtained for each spatial frequency. Sharpness of a photographic combination greatly depends of the contrast of the silver halide photographic material and the sharpness of the intensifying screen used therein.

The radiographic intensifying screen used in this invention comprises a support having thereon a phosphor layer containing a phosphor and a protective layer, in which the content of a binder in the phosphor layer is preferably 0.1 to 5% by weight, based on the phosphor layer. Further, the binder preferably contains a resin having a hydrophilic polar group.

The phosphor layer generally comprises phosphor particles, a binder and voids. The void refers to a space in the phosphor layer, in which neither a phosphor particle nor a binder exists. The volumetric proportion of voids in the phosphor layer increases with a decrease of the binder. The voids act as a factor of light scattering., preventing diffusion of emission from the phosphor particles and enhancing sharpness. In cases when the content of the binder in the phosphor layer exceeds 5.0%, voids in the layer decrease to reduce light scattering, making easier diffusion of the emission light and leading to deteriorated sharpness of images. In cases when the binder content is less than 0.1%, it becomes difficult for the binder to broadly cover surfaces of phosphor particles and an essential function of the binder having phosphor particles bound with each other becomes more difficult, leading to reduction in the filling factor of the phosphor. Further, it becomes difficult for the binder to be uniformly distributed over the entire layer, leading to non-uniform emission and deteriorated graininess of images. The phosphor layer also becomes brittle, resulting in undesired abrasion marks.

The phosphor particle size was determined by dispersing phosphor particles in water, along with a surfactant, using a light scattering particle size measurement apparatus (e.g., LA-910 available from Horiba Seisakusho Co. Ltd.). The average size of phosphor particles used in this invention is preferably not less than 2 μm and not more than 7 μm. The filling factor of a phosphor in the phosphor layer is defined based on the following equation:

$$\text{Filling factor} = [O \div (P \times Q \times R)] \times 100$$

wherein O represents the weight (g) of the phosphor obtained in such a manner that the protective layer of a radiographic intensifying screen is removed, the entire phosphor layer is dissolved out using an organic solvent, filtered, dried and calcined using an electric furnace at 600° C. for 1 hr. to remove any resin on the surface; P represents the thickness (cm) of the phosphor layer before being dissolved out; Q represents an area (cm$^2$) of the screen used in dissolving-out, and R represents the density (g/cm$^3$) of the phosphor. The filling factor is preferably not less than 60%.

Examples of binders used in this invention include polyurethane, vinyl chloride copolymer, vinyl chloride-vinyl acetate copolymer, vinyl chloride-vinilidene chloride copolymer, vinyl chloride-acrylonitrile copolymer, butadiene-acrylonitrile copolymer, polyamide, polyvinyl butyral, cellulose derivative (e.g., nitrocellulose), styrene-butadiene copolymer, a variety of types of synthetic rubber resin, phenol resin, epoxy resin, urea resin, melamine resin, phenoxy resin, silicone resin, acryl resin and urea-formamide resin. Among these, polyurethane-polyester, vinyl chloride type copolymer, polyvinyl butyral and nitrocellulose are preferably used. The average molecular weight of the binder is preferably 5,000 to 200,000.

The binder preferably contains a resin containing a hydrophilic polar group. In this case, the hydrophilic polar group improves dispersion of the phosphor particles, through its adsorption to the surface of the particles, leading to prevention of coagulation of the phosphor particles and enhancement of coating stability, sharpness and graininess.

The resin containing a hydrophilic polar group is one containing a hydrophilic polar group selected from the group consisting of —$S_3M$, —$OS_3M$, —COOM,—PO(OM')$_2$, and —OPO(OM')$_2$ (i.e., negative functional group), in which M is hydrogen atom or an alkali metal atom such as Li, K, Na.

As a preferred example of the resin containing the hydrophilic polar group, polyurethane is explained further in detail. Polyurethane can be synthesized through reaction of a polyol with a polyisocyanate which is generally employed. As a polyol component is generally used polyesterpolyol which can be obtained through reaction of the polyol with a polybasic acid. According to this known method, the polyesterpolyol containing the hydrophilic polar group can be synthesized by using the polybasic acid containing the hydrophilic polar group, as a part of the polybasic acid.

Examples of the polybasic acid include phthalic acid, isophthalic acid, terephthalic acid, adipic acid, azelaic acid, cebacic acid and maleic acid. Examples of the polyesterpolyol containing the hydrophilic polar group include , 5-sulfoiso-phthalic acid, 2-sulfoisophthalic acid, 4-sulfoisophthalic acid, 3-sulfoisophthalic acid, dialkyl 5-sulfoisophthalate, dialkyl 2-sulfoisophthalate, dialkyl 4-sulfoisophthalate, dialkyl 3-sulfoisophthalate and their sodium or potassium salt. Examples of the polyol include trimethylol propane, hexanetriol, glycerin, trimethylolethane, neo-pentylglycol, pentaerythritol, ethylene glycol, propylene glycol, 1,3-butanediol, 1,4-butanediol, 1,6-hexanediol, diethylene glycol and cyclohexanedimethanol.

Polyesterpolyols containing other hydrophilic polar groups can also be synthesized by a conventionally known method. The polyurethane can be prepared by using these polyesterpolyol as a raw material for the synthesis.

Examples of the polyisocyanate include diphenylmethan-4,4-diisocyanate (MDI), hexamethylene diisocyanate (HMDI), tolylene diisocyanate (TDI), 1,5-naphthalene diisocyanate (NDI), toluidine diisocyanate (TODI), lysine isocyanate methyl ester (LDI) and isopolodiisocyanate (IPDI). As another method for synthesizing the polyurethane, it can be prepared through addition reaction of the following compound containing the hydrophilic polar group and a chlorine atom to a polyurethane containing a OH group.

$ClCH_2CH_2SO_3M$
$ClCH_2CH_2OSO_3M$
$ClCH_2PO\ (OM')_2$
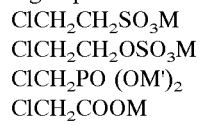

The introduction of a hydrophilic polar group into the polyurethane is known in the art. Furthermore, there are also commercially available polyurethane containing —$SO_3Na$ group, UR8300)product by Toyobo Co. Ltd.) and polyurethane containing —COOH group. TIM-6001 (product by Sanyo Kasei Co. ltd.).

In addition to the resins above-described, the following resins are usable as a binder containing the hydrophilic polar group. Examples thereof are one having a weight-averaged molecular weight of 5,000 to 200,000, including a vinyl chloride copolymer, vinyl chloride-vinyl acetate copolymer, vinyl chloride-vinylidene chloride copolymer, butadiene-acrylonitrile copolymer, polyamide, poly(vinyl butylal), cellulose derivative (e.g., nitrocellulose), styrene-butadiene copolymer, a variety of synthetic rubber type resins, phenol resin, epoxy resin, urea resin, melamine resin, pheoxy resin, silicone resin, acryl type resin, urea-formamide resin. Among these are preferred a polyester, vinyl chloride type copolymer poly(vinyl butyral) and nitrocellulose.

The vinyl chloride type resin can be synthesized through addition reaction of the following compound containing a hydrophilic polar group and a chlorine atom to a copolymer containing an OH group such as vinyl chloride-vinyl alcohol copolymer:

$ClCH_2CH_2SO_3M$
$ClCH_2CH_2SO_3M$
$ClCH_2PO(OM')_2$
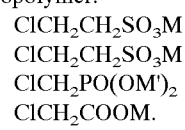

Alternatively, copolymerization can be done by using copolymerizable monomers. Thus, a reactive unsaturated monomer having a repeating unit with a hydrophilic polar group is introduced into a reaction vessel such as an autoclave with a given volume and polymerization can be done by using a conventional polymerization initiator including radical polymerization initiator such as benzoyl peroxide (BPO) and azobisisobutyronitrile (AIBN), redox polymerization initiator, anionic polymerization initiator and cationic polymerization initiator. Examples of the reactive monomer for introducing a sulfonic acid or its salt include unsaturated hydrocarbon sulfonic acids such as vinyl sulfonic acid, acrylsulfonic acid and p-styrenesulfonic acid and its salts. Furthermore, acryl or methacrylsulfoalkyl ester such as 2-acrylamido-2-methylpropanesulfonic acid, (metha)acrylsulfonic acid ethyl ester, (metha)acrylsulfonic acid propyl ester and their salts and ethyl 2-sulfoacrylate are cited. In cases where a carboxylic acid or its salt (i.e. —COOM group) is introduced, (metha)acrylic acid or maleic acid may be usable. In cases where phosphoric acid or its salt is introduced, (metha)acrylic acid-2-phosphoric acid ester may be usable.

Introduction into the hydrophilic polar group to a vinyl chloride copolymer is commonly known in the art. As commercially available products of these compounds are cited, for example, vinyl chloride-vinyl acetate copolymer containing —$SO_3K$ group, MR110 (produced by Nihon Zeon Co. Ltd.) and polyester containing —$SO_3Na$ group, Biron 280 (produced by Toyobo Co. Ltd.).

The hydrophilic polar group can be identified by means of, e.g., NMR (Nuclear Magnetic Resonance) and quantitatively determined by wavelength-dispersion type fluorescent X-ray analysis (WDX). As an exemplary means of measuring the content of the hydrophilic polar group, the content of an $SO_3M$ group can be determined according to the following manner. Various amounts of sulfur (S) at a purity of 99.9999% are added to a matrix resin, with a given amount of a phosphorus (P)-containing compound as an internal standard material. Fluorescent X-ray intensities of S to P are measured with respect to each sample by the WDX to prepare a calibration curve for the content of sulfur. Next, to a sample is added a given amount of P-containing compound, which was subjected to WDX analysis to determine the P-content. The content of the hydrophilic polar group is preferably $10^{-7}$ to $10^{-3}$ mol, and more preferably $10^{-7}$ to $10^{-4}$ mol per g of a binder contained in the phosphor layer.

A resin not containing a hydrophilic polar group may be contained in the binder. Examples of the resin are one having a weight-averaged molecular weight of 5,000 to 200,000, including urethane-vinyl chloride copolymer, vinyl chloride-vinyl acetate copolymer, vinyl chloride-vinilidene chloride copolymer, vinyl chloride-acrylonitrile copolymer, butadiene-acrylonitrile copolymer, polyamide, polyvinyl butyral, cellulose derivative (e.g., nitrocellulose), styrene-butadiene copolymer, a variety of types of synthetic rubber resin, phenol resin, epoxy resin, urea resin, melamine resin, phenoxy resin, silicone resin, acryl resin and urea-formamide resin. Among these, polyurethane-polyester, vinyl chloride type copolymer, polyvinyl butyral and nitrocellulose are preferably used. In this case, the content of the hydrophilic polar group is preferably $10^{-7}$ to $10^{-3}$ mol per g of the binder contained in the phosphor layer.

Examples of preferred phosphors used in the radiographic intensifying screen include the following: tungstate phosphor (e.g., $CaWO_4$, $MgWO_4$, $PbWO_4$, etc.); terbium activated rare earth sulfide phosphor (e.g., $Y_2O_2S$:Tb, $Gd_2O_2S$:Tb, $La_2O_2S$:Tb, $(Y.Gd)_2O_2S$:Tb, $(Y.Gd)_2O_2S$:Tb.Tm, etc.); terbium activated rare earth phosphate phosphor (e.g.,$YPO_4$:Tb, $GdPO_4$:Tb, $LaPO_4$:Tb etc.); terbium activated rare earth oxyhalide phosphor (e.g.,LaOBr:Tb, LaOBr:Tb. Tm, LaOCl:Tb, LaOCl:Tb.Tm, LaOCl:Tb.Tm, LaOBr:Tb, GdOBr:Tb, GdOCl:Tb, etc.); thulium-activated rare earth oxyhalide phosphor (e.g., LaOBr:Tm, LaOCl:Tm); barium sulfate phosphor (e.g., $BaSO_4$:Pb, $BaSO_4$:$Eu^{2+}$, $(Ba.Sr)SO_4$:$Eu^{2+}$); bivalent europium activated alkali earth metal phosphate phosphor [e.g., $(Ba_2PO_4)_2$:$Eu^{2+}$, $(Ba_2PO_4)_2$:$Eu^{2+}$, etc.); bivalent europium activated alkali earth metal fluorohalide phosphor [e.g., $BaFCl$:$Eu^{2+}$, $BaFBr$:$Eu^{2+}$, $BaFCl$:$Eu^{2+}$.Tb, $BaFBr$:$Eu^{2+}$.Tb, $BaF_2BaClKCl$:$Eu^{2+}$, $(Ba\ Mg)F_2BaClKCl$:$E^{2+}$ etc.]; iodide phosphor (e.g., CsI:Na, CsI:Tl, NaI, KI:Tl); sulfide phosphor [ZnS:Ag, (Zn Cd)S:Ag, (Zn Cd)S:Cu, (Zn Cd)S:Cu.Al]; hafnium phosphate phosphor (e.g., $HfP_2O_7$:Cu); tantalate phosphor (e.g.,. $YTaO_4$, $YTaO_4$:Tm, $YTaO_4$:Nb, [Y Sr]$TaO_{4-x}$:Nb, $LuTaO_4$, $LuTaO_4$:Nb, (Lu Sr)$TaO_{4-x}$:Nb, $GdTaO_4$:Tm, $Gd_2O_3TaO_4$:Tm, $Gd_2O_3Ta_2O_5B_2O_3$:Tb]. However, phosphors usable in the invention are not to these compounds. Any phosphor capable of emitting visible or near-ultra violet light upon exposure to radiation, may be usable.

As to a method for preparing the radiographic intensifying screen, first one is that a coating solution of the phosphor comprised of a binder and the phosphor (hereinafter referred to as a phosphor coating solution) is coated on a support to form a phosphor layer. A second one is that a sheet comprised of the binder and phosphor is formed and then put onto the support, followed by a process of adhesion to the support at not lower than a softening or melting temperature of the binder. As a method for forming the phosphor layer on the support are cited the above two types of methods. However, any method whereby the phosphor layer is uniformly formed on the support, may be adopted. Impingement coating may be usable. In the first preparing method, the phosphor layer is formed by coating a coating solution in which the phosphor is homogeneously dispersed in a binder, on the support and drying it. In the second preparing method, on the other hand, the phosphor sheet which is to form the phosphor layer is prepared by temporarily coating a coating solution of the phosphor on a support or subbed support and drying, followed by peeling the layer off from the support. Thus, the binder and phosphor particles are added in an appropriate solvent and mixed with stirring by means of a disperser or a ball mill to form a coating solution in which the phosphor is homogeneously dispersed in the binder.

Examples of the solvent for the coating solution include lower alcohols such as methanol, ethanol, n-propanol and n-butanol; chloro-containing hydrocarbons such as methylene chloride and ethylene chloride; ketones such as acetone, methyl ethyl ketone and methyl isobutyl ketone; cyclic hydrocarbon compounds such as toluene, benzene, cyclohexane, cyclohexanone and xylene; esters of a lower fatty acid and lower alcohol, such as methyl acetate, ethyl acetate and butyl acetate; and ethers such as dioxane, ethylene glycol monomethyl ester, ethylene glycol monoethyl ester.

The coating solution may contain a dispersing agent and plasticizer for the purpose of enhancement of dispersion of the phosphor or binding power between the binder and phosphor after forming the layer, respectively. Examples of the dispersing agent include phthalic acid, stearic acid, caproic acid and a hydrophobic surfactant. Examples of the plasticizer include phosphate esters such as triphenyl phosphate, tricresyl phosphate and diphenyl phosphate; phthalate esters such as diethyl phthalate and dimethoxyethyl phthalate; glycolate esters such as ethyl phthalylethyl glycolate and butyl phthalylbutyl glycolate; polyesters of polyethylene glycol and dibasic fatty acid, such as polyester of triethylene glycol and adipic acid and polyester of diethylene glycol and succinic acid.

The thus-prepared coating solution containing the phosphor and binder is uniformly coated on the temporary support to form a coating layer of the coating solution. A means for coating is, for example, a doctor blade, roll coater, knife-coater, extrusion coater and so forth.

Support or temporary support made of glass, wool, cotton, paper or metal may be usable and those which are capable of being converted in the form of flexible sheet or roll are preferred in terms of handleability as information recording material. In view thereof are preferred plastic films such as cellulose acetate film, polyester film, polyethylene terephthalate film, polyamide film, polyimide film, triacetate film and polycarbonate film; metal sheets such as aluminum foil and aluminum alloy foil; and paper including paper for general use, paper for use in printing such as coated paper and art paper, photographic base paper such as baryta paper and resin-coated paper, paper sized with polysaccharide as described in Belgian Patent 784,615, pigment paper containing pigment such as titanium dioxide, and paper sized with poly(vinyl alcohol).

In the second preparing method, coat on a temporary support or subbed-support is peeled off from the support to form a phosphor layer sheet. Therefore, it is preferred that the surface of the support is previously coated with a releasing agent so that the phosphor layer is easily peelable. To strengthen binding between the support and phosphor layer, a sub layer may be provided by coating polyester or gelatin on the surface of the support to enhance adhesion. There may be provided a light-reflecting layer comprised of light-reflecting material such as titanium dioxide or a light-absorbing layer comprised of light-absorbing material such as carbon black, for the purpose of enhancement of sensitivity and image quality (e.g., sharpness, graininess, etc.). The constitution thereof can be selected according to its purpose, usage and the like. Black-tinted polyethylene terephthalate support containing carbon black is specifically preferred.

The phosphor layer according to the invention may be compressed. Compression of the phosphor layer leads to an increase of a filling density of the phosphor and improvements in sharpness and graininess. Compression can be made by the use of a pressing machine or calendering roll. In the case of the first preparing method, the phosphor and support are compressed together as such. In the case of the second preparing method, the obtained phosphor sheet is put on the support and compressed at not lower than a softening temperature or melting temperature of the binder to cause the phosphor sheet to adhere to the support. Thus, the phosphor sheet can be expanded to further thinner thickness by employing the method of compression-adhering, instead of previously fixing the sheet to the support.

Conventionally, the radiographic intensifying screen and the radiographic image converting panel each have a transparent protective layer provided on the surface of the phosphor layer for physical and chemical protection thereof. In the invention, the transparent protective layer is preferably provided. The thickness thereof is in general within a range of 2 to 20 $\mu$m.

The transparent protective layer can be formed by coating, on the surface of the phosphor layer, a solution prepared by dissolving in an appropriate solvent a cellulose derivative such as cellulose acetate or nitrocellulose, or a synthetic polymer material such as polymethyl methaacrylate, polyethylene terephthalate, poly(vinyl butyral), poly(vinyl formal), polycarbonate, poly(vinyl acetate), copoly(vinyl chloride.vinyl acetate). These polymer materials may be used singly or in combination thereof. In cases when coating the protective layer, a cross-linking agent may be added thereto immediately before coating.

The protective layer may be formed by adhering a sheet comprised of poly(ethylene terephthalate), poly(ethylene naphthalate), polyethylene, poly(vinilidene chloride) or polyamide with an adhesive.

The protective layer according to the invention is preferably formed with a coating layer containing an organic solvent-soluble fluoro resin. The fluoro resin is referred to as fluorine containing olefin (i.e., fluoroolefin) polymer or copolymer having as a copolymerizing component a fluorine containing olefin. The protective layer formed of fluoro resin coating may be cross-linked. The fluoro resin coating protective layer has such an advantage that stain due to fat resulted from touching with hands or photographic materials, or due to plasticizer bled out of the photographic material is not liable to penetrate into the internal portion of the protective layer, so that the stain can easily be wiped off. The fluoro resin may be used in combination with another polymer material for the purpose of improving layer strength.

The protective layer is preferably a transparent synthetic resin layer with a thickness of 10 $\mu$m or less and provided on the phosphor layer. The use of such a thin protective layer, particularly in the case of the intensifying screen, shortens the distance from the phosphor to a silver halide emulsion layer, contributing to improvement in sharpness of the resulting radiographic image. The phosphor layer may be tinted with a color having an absorption within the emission wavelength of the phosphor (such as red or yellow) to enhance sharpness. The thickness of the phosphor layer is preferably 50 to 400 $\mu$m, and more preferably 100 to 300 $\mu$m.

Silver halide photographic materials used in this invention preferably exhibit a sensitivity of 1.0 to 3.0 and an average contrast of 2.5 to 4.5. Sensitivity of a silver halide photographic material is represented by a relative value, based on the sensitivity of silver halide photographic material CMH being 1.0 when used in combination with radiographic intensifying screen MD100. With regard to the measurement of sensitivity, a screen-film system is exposed to X rays which has been generated from a molybdenum target tube operated at three-phase electric power source of 28 kVp and transmitted through a 1 mm beryllium filter, 0.03 mm molybdenum filter and 2 cm acryl filer and further subjected to photographic processing. The processing was carried out at 34° C. for a period of 90 sec. with developer XD-SR, fixer XF-SR (each of which is available from Konica Corp.), using automatic processor SRX-502, available from Konica Corp. A characteristic curve is made by the distance method and sensitivity is represented by the reciprocal of an exposure dose necessary to give a density of 1.0 plus a fog density. The average contrast is a slope of a line connecting a point at a density of 0.25 plus a fog density and a point at a density of 2.0 plus a fog density.

The silver halide photographic material used in this invention preferably is one which has a silver halide emulsion layer on one side of a subbed, 100 to 200 $\mu$m thick, blue-tinted polyethylene terephthalate support and a gelatin layer as a backing layer on the other side of the support. The backing layer is preferred in terms of anti-curling. It is preferred to subject to a matting treatment to prevent blocking of films. It is a preferred embodiment to contain an antistatic agent or antihalation agent. In one preferred embodiment, this photographic film is in a sheet form and rounded at its corners to prevent an injury, and a notch is put to recognize the emulsion side. In the enlarging mammography, a photographic film of a size 8×10 inches or more is preferably employed to obtain an entire image of a mamma.

The single-sided coated silver halide photographic material used in this invention may have a single emulsion layer or two or more layers differing in average grain size. The relation ship of sensitivity between layers is not specifically limited. In the case of comprising upper and lower layers, for example, the sensitivity of the upper layer may be higher than that of the lower layer, or vice versa. It may be optimally designed according to the purpose of diagnosis.

Silver halide grains contained in the emulsion layer of the silver halide photographic material used in this invention preferably comprise silver iodobromide. The iodide content of the grain is preferably not more than 2 mol %. The shape of silver halide grains may be a cubic, octahedral, or tabular form. Silver halide grains may be a single form or a mixture thereof. In the case on tabular grains, the average aspect ratio is preferably not less than 2 and less than 15. The silver halide grains are preferably monodisperse, and a blend of monodisperse emulsions may be used. The silver halide grains are subjected to chemical sensitization such as sulfur sensitization or selenium sensitization. The silver halide grains may be doped with a metal ion such as iridium cation or may be added with a spectral sensitizing dye during the stage of forming the silver halide grains.

In a silver halide emulsion used in the invention, various additives may be incorporated. As the additives can be employed compounds as described in RD Nos. 17643 (December, 1978), 18716 (November, 1979) and 308119 (December, 1989), wherein relevant types of compounds and sections thereof are follows:

|  | RD-17643 | | RD-18716 | RD-308119 | |
|---|---|---|---|---|---|
| Additive | Page | Sec. | Page | Page | Sec. |
| Chemical sensitizer | 23 | III | 648 upper right | 996 | III |
| Sensitizing dye | 23 | IV | 648–649 | 996–8 | IVA |
| Desensitizing dye | 23 | IV | | 998 | IVB |
| Dye | 25–26 | VIII | 649–650 | 1003 | VIII |
| Developing accelerator | 29 | XXI | 648 upper right | | |
| Antifoggant/stabilizer | 24 | IV | 649 upper right | 1006–7 | VI |
| Brightening agent | 24 | V | | 998 | V |
| Hardening agent | 26 | X | 651 left | 1004–5 | X |
| Surfactant | 26–27 | XI | 650 right | 1005–6 | XI |
| Antistatic agent | 27 | XII | 650 right | 1006–7 | XIII |
| Plasticizer | 27 | XII | 650 right | 1006 | XII |
| Lubricant | 27 | XII | | | |
| Matting agent | 28 | XVI | 650 right | 1008–9 | XVI |
| Binder | 26 | XXII | | 1003–4 | IX |
| Support | 28 | XVII | | 1009 | XVII |

Examples of supports usable in the photographic materials relating to the invention include those described in afore-mentioned RD-17643, page 28 and RD-308119, page 1009.

To provide rapid processability, the silver halide photographic material may be added with a hardening agent to adjust the aqueous swelling ratio in the course of development, fixing and washing so as to reduce a water content before drying. The swelling ration after development is preferably 150 to 250% and the swollen layer thickness is preferably not more than 70 $\mu$m. The aqueous swelling ratio of not more than 250% results in superior dryability, leading to enhanced transportability in processing by an automatic processor, specifically, in rapid processing. The aqueous swelling ratio of more than 250% results in undesired development unevenness or residual color stain. The aqueous swelling ratio refers to the difference in thickness between a layer swollen in the processing solutions and a layer before processing, divided by the layer thickness before processing and times 100(%).

Solid processing composition may be in the form of powder, a tablet, pellet or granules. The solid processing composition, if necessary, may be subjected to moisture-proof treatments. In the invention, the powder refers to an aggregate of fine crystals and the granules refer to those prepared by subjecting the powder to granulation treatments and with granular size of 50 to 5000 $\mu$m. The tablet refers to those prepared by subjecting the powder or granules to compression-molding to a given form.

To reduce variation of photographic performance, it is effective to reduce an open top area of a developer in an automatic processor. The open top area is preferably not more than 80 cm$^2$/l. When the open top area is not more than 80 cm$^2$/l, undissloved solid processing composition or a concentrated solution formed immediately after dissolution is not easily formed. The open top are represented as an area in contact with air per unit volume of a processing solution, in terms of cm$^2$/l. The open top area is preferably not more than 80 cm$^2$/l more preferably 3 to 50 cm$^2$/l, and still more preferably 10 to 35 cm$^2$/l. The open top are can be reduced by using an air-shielding resin as a floating cover or by using a slit type processor described in JP-A 63-131138, 63-216050 and 63-235940.

The solid developing or fixing composition can be used as not only a developer or fixer but also a photographic processing chemicals such as a rinsing agent. Particularly when used as a developer or fixer, effects of stabilizing photographic performance are marked. A processing chemical having at least a part solidified and a solid processing chemical each applicable to the invention are included in the scope of the invention. It is, however, preferable that the whole component of these processing chemicals are solidified. It is also preferable that the components thereof are each molded into a separate solid processing chemical and then individually packed in the same form. It is further preferable that the components are packed in series in the order of periodically and repeatedly adding them from the packages.

As for the means for supplying a solid processing chemical to a processing tank in the invention, and in the case where the solid processing chemical is of the tablet type, for example, there are such a well-known means as described in Japanese Utility Model OPI Publication Nos. 63-137783/1988, 63-97522/1988 and 1-85732/1989, wherein, in short, any means may be used, provided that at least a function for supplying a tableted chemical to a processing tank can be performed. And, in the case where the solid processing chemical is of the granulated or powdered type, there are such a well-known means such as the gravity dropping systems described in JP OPI Publication Nos. 62-81964/1987, 63-84151/1988 and 1-292375/1989, and the screw system described in JP OPI Publication Nos. 63-105159/1987 and 63-84151/1988. However, the invention shall not be limited to the above-given well-known means.

A solid processing composition of the invention may be added to any position inside a processing tank and, preferably, to a position communicated with a section for processing a light-sensitive material and circulating a processing solution between the processing tank and the processing section. It is also preferable to have such a structure that a certain amount of processing solution can be circulated therebetween so that a dissolved component can be moved to the processing section. It is further preferable that a solid processing chemical is added to a thermostatically controlled processing solution.

The developer used in the invention preferably contains, as a developing agent, dihydroxybenzenes described in JP-A 6-138591 (page 19–20), aminophenols, pyrazolidones or reductones described in JP-A 5-165161. Of the pyrazolidones, 4-substituted ones (e.g., dimezone, dimezone S) are water soluble and their solid composition is superior in aging stability.

The developing solution used in the invention may contain, as a preservative, an organic reducing agent as well as a sulfite described in JP-A 6-138591. Further, a bisulfite adduct of a hardening agent described in Japanese Patent Application No. 4-586323 is also usable. Compounds described in JP-A 5-289255 and 6-308680 (general formulas 4-a and 4-b) may be contained as an antisludging agent. Addition of a cyclodextrin compound is preferred, particularly as described in JP-A 1-124853. An amine compound may be added to the developing solution, as described in U.S. Pat. No. 4,269,929.

A buffering agent may be used in the developing solution, including sodium carbonate, potassium carbonate, potassium bicarbonate, trisodium phosphate, tripotassium phosphate, dipotassium phosphate, sodium borate, potassium borate, sodium tetraborate, potassium tetraborate, sodium o-hydroxybenzoate (sodium salicylate), potassium o-hydroxybenzoate (potassium salicylate), sodium 5-sulfo-2-hydroxybenzoate (sodium salicylate) and potassium 5-sulfo-2-hydroxybenzoate (potassium salicylate).

There can be added, as a development accelerating agent, thioether compounds described in JP-B 37-16088, 37-5987, 38-7826, 44-12380 and 45-9019 (herein, the term, "JP-B"

means a published Japanese Patent) and U.S. Pat. No. 3,813,247; p-phenylenediamine compounds described in JP-A 52-49829 and 50-15554; quaternary ammonium salts described in JP-B 44-30074, JP-A 50-137726, 56-156826 and 52-43429; p-aminophenols described in U.S. Pat. Nos. 2,610,122, and 4,119,462; amine compounds described in U.S. Pat. Nos. 2,494,903, 3,128,182, 4,230,796, 3,253,919, 2,482,546, 2,596,926 and 3,582,346 and JP-B 41-11431; polyalkylene compounds described in JP-B 37--16088, 42-25201, 41-11431 42-23883, U.S. Pat. No. 3,128,183, 3,532,501; 1-phenyl-3-pyrazolidones; hydrazines, mesoion type compound and imidazoles.

Alkali metal halides such as potassium iodide are used as a antifoggant. Organic antifoggants include benzotriazole, 6-nitrobenzimidazole, 5-nitrobenzimidazole, 5-methylbenzotriazole, 5-nitrobenzotriazole, 5-chlorobenzotriazole, 2-thiazolyl-benzimidazole, 2-thiazolylmethyl-benzimidazole, indazole, hydroxyazaindolizine, adenine and 1-pheny-5-mercaptotetrazole.

In the developer composition used in the invention, methylcellosolve, methanol, acetone, dimethylformamide, cyclodextrin compounds and compounds described in JP-B 47-33378 and 44-9509 can be employed as an organic solvent to enhance solubility of the developing agent. Furthermore, various additives such as an anti-staining agent, anti-sludging agent and interlayer effect-accelerating compound are optionally added.

In a fixed used in the invention are incorporated known compounds usable in a fixer, such as a fixing agent, chelating agent, pH buffer, hardening agent, preservative, as described in JP-A 4-242246 (page 4) and 5-113632 (pages 2–4). Further are usable hydrosulfite adduct of a hardening agent, as a hardening agent and known fixing accelerators.

It is preferred to add a starter prior to processing. A solidified starter is also preferred. An organic acid such as polycarboxylic acid compound, alkali earth metal halide, organic restrainer or development accelerator is used as a starter. In developer solutions used for processing silver halide black-and-white photographic materials, hydroquinones are generally employed as a developing agent, however, a developer solution substantially not containing hydroquinones, for example a developer solution containing ascorbic acid, se described in U.S. Pat. No. 5,236,816 may be used from the point of view of safety in working and environment protection.

The developing time of the silver halide photographic material is preferably 3 to 90 sec., and more preferably 5 to 60 sec; and the total processing time (i.e., Dry to Dry) is preferably 15 to 210 sec., and more preferably 15 to 90 sec.

EXAMPLES

1. Preparation of Radiographic Intensifying Screen

Binders of polyurethane and nitrocellulose, and a dispersing agent of diethyl phthalate were dissolved in a mixed solvent of methyl ethyl ketone and toluene, and mixed with the resulting solution was terbium-activated gadolinium oxysulfide phosphor ($Gd_2O_2S$:Tb) having an average particle size of 3.1 $\mu$m to 10 $\mu$m so that the phosphor filling factor was within the range of 55 to 66% and the proportion of the binder was 0.08% or 1.5%. The resulting mixture was coated on a 250 $\mu$m thick polyethylene terephthalate film using a knife coater and dried to form a phosphor layer. Then, a polyester type adhesive was coated on one side of 9 $\mu$m thick polyethylene terephthalate film and the adhesive side of the film was brought into contact to the phosphor layer to form a protective layer on the phosphor layer to obtain a radiographic intensifying screen. The thus obtained intensifying screens are shown in Table 1 with respect to the phosphor particle size, phosphor filling factor and percentage by weight of the binder, based on the phosphor.

Screens M and N were prepared by replacing a part of the binder with polyurethane UR8300 (available from TOYOBO Co., Ltd.) so that —$SO_3Na$ group was contained in an amount of $5 \times 10^{-5}$ mole equivalent per g of binder.

2. Preparation of Photographic Material Film

To a fine silver iodobromide seed grain emulsion having (111) twin planes and an average circular equivalent diameter of 0.20 $\mu$m and containing 0.2 mol % iodide, an aqueous silver nitrate solution and an aqueous solution of potassium bromide and potassium iodide were added by the double jet addition to obtain tabular silver iodobromide grains containing 0.2 mol % iodide. From scanning-type electron micrograph, it was proved that the tabular grains were comprised of hexagonal grains including trigonal grains in part, having an average circular equivalent diameter of 1.21 $\mu$m (a coefficient of variation of 16.3%) and a thickness of 0.18 $\mu$m. Spectral sensitizing dye 5,5'-dichloro-9-ethyl-3.3'-di-(3-sulfopropyl)-oxacarbocyanine sodium salt was added during the grain formation. The emulsion was desalted to remove soluble salts and subjected to gold-sulfur sensitization, and thereto was added 4-hydroxy-6-methyl-1, 3,3a, 7-tetrazaindene. In an aqueous gelatin solution were dissolved t-butylcatecol, 1-phenyl-5-mercaptotetrazole and sodium 2-mercaptobenzimidazole-5-sulfonate and to this solution, the obtained silver halide emulsion was added to obtain a coating solution. The coating solution was coated on a blue-tinted, 175 $\mu$m thick polyethylene terephthalate film having a back layer and further thereon, an aqueous gelatin solution for a protective layer, containing a matting agent and a surfactant was simultaneously coated and subsequently dried. The thus prepared photographic material was cut to a size of 8×10 inches to obtain Film a.

Similarly, tabular silver iodobromide grain emulsions containing 0.2 mol % iodide and an average grain diameter different from that of the foregoing emulsion were prepared, provided that the amount of the seed grain emulsion was optimally varied and the addition time of silver nitrate and halide solutions was also varied. The thus prepared emulsions were each subjected to gold-sulfur sensitization and after incorporating additives, were coated together with a protective layer solution to obtain desired films. Thus, it was proved that Film b, c, d and e each contained silver halide grains having an average diameter of 1.41, 1.55, 0.88 and 1.8 $\mu$m, and a thickness of 0.21, 0.23, 0.13 and 0.27 $\mu$m, respectively. Film f was similarly prepared, provided that the silver halide emulsion used in Film a and silver halide emulsions used in Films d and e were mixed to adjust the contrast. Film g was prepared by coating the emulsion used in Film d as an upper layer and the emulsion used in Film a as a lower layer.

3. Determination of Sensitivity of Film ($S_2$)

Radiographic intensifying screen MD100 (available from Konica Corp.) was combined with mammographic film CMH (available from Konica Corp.) or Films a through g to determine the sensitivity of these films (denoted as $S_2$). Rotary anode X ray tube Rotanode DRX-B1146B-Mo (available from Toshiba Electric Co. Ltd.) was employed. This X ray tube (molybdenum target tube) was operated at 28 kVp of a three phase power source, and each of the films was exposed to X ray transmitted through 1 mm thick beryllium, 0.03 mm thick molybdenum and 2 cm thick acryl filters, from the film side. The distance between the X ray tube and the screen-film combination was 60 cm. The X ray dose was adjusted by varying the mAs value of the X ray tube. Each of the exposed films was subjected to photographic processing at 34° C. for 90 sec., using automatic processor SRX-502 (available from Konica Corp.) with developer XD-SR and fixer XF-SR (both available from Konica Corp.). Herein, the sensitivity of the film is represented by a relative value of the reciprocal of an X ray exposure amount necessary to give a density of 1.0 plus a fog density, based on the sensitivity of the CMH film being 1.

4. Determination of Sensitivity of Intensifying Screen ($S_1$)

Radiographic intensifying screen MD100 (available from Konica Corp.) or each of screens A through O obtained above was combined with mammographic film CMH (available from Konica Corp.). Rotary anode X ray tube Rotanode DRX-B1146B-Mo (available from Toshiba Electric Co. Ltd.) was employed. This X ray tube (molybdenum target tube) was operated at 28 kVp of a three phase power source, and each of the films was exposed to X ray transmitted through 1 mm thick beryllium, 0.03 mm thick molybdenum and 2 cm thick acryl filters, from the film side. The distance between the X ray tube and the screen-film combination was 60 cm. The X ray dose was adjusted by varying the mAs value of the X ray tube. Each of the exposed films was subjected to photographic processing at 34° C. for 90 sec., using automatic processor SRX-502 (available from Konica Corp.) with developer XD-SR and fixer XF-SR (both, available from Konica Corp.). Herein, the sensitivity of each of screens A through O (denoted as $S_1$) was represented by a relative value of the reciprocal of an X ray exposure amount necessary to give a density of 1.0 plus a fog density, based on the sensitivity of the MD100 screen being 100.

5. Determination of Sensitivity ($S_3$) and Contrast of Combination

Sensitivity of the combination of a screen and a film was determined similarly to the above-described determination of the film sensitivity. Thus, screen-film combinations as shown in Table 1 were each exposed to X ray and processed similarly to the foregoing, and the sensitivity of each of the combinations was represented by a relative value of the reciprocal of an X ray exposure amount necessary to give a density of 1.0 plus a fog density, based on the speed of the combination of MD100 and CMH being 100. Further, the combinations were similarly subjected to X ray exposure to determine the contrast. Thus, a characteristic curve was prepared by the so-called distance method, in which the X ray exposure amount was varied by varying the distance between the X ray tube and the combination. The contrast was determined from the slope of a line connecting a point corresponding to a density of 0.25 plus a fog density and a point corresponding to a density of 2.0 plus a fog density on the characteristic curve.

6. Determination of CTF of Intensifying Screen

Radiographic film CMH (available from Konica Corp.) and each of intensifying screens A through O were combined, and a rectangular chart for use in MTF measurement (Type 9 produced by Kasei Optonics Corp., made of 40 μm thick tin, and spatial frequency of 0 to 10 lines) was brought into contact with the film side of the combination and exposed to X ray. Each of the exposed films was subjected to photographic processing at 34° C. for 90 sec., using automatic processor SRX-502 (available from Konica Corp.) with developer XD-SR and fixer XF-SR (both available from Konica Corp.). The thus obtained chart image was subjected to densitometry with scanning, using microdensitometer PDM 6 (available from Konica Corp.). From the obtained density profile, densities of the peak and valley of a rectangular wave for each frequency were measured to determine the contrast for each frequency. The thus obtained contrasts were normalized to a contrast at a frequency of zero to determine CTF.

7. Evaluation of Identifying Capability

A rotary anode X ray tube Rotanode DRX-B1146B-Mo (available from Toshiba Electric Co. Ltd.) was employed. This X ray tube (molybdenum target tube) was operated at 28 kVp of a three phase power source, and each of the films was exposed to X ray transmitted through 1 mm thick beryllium, 0.03 mm thick molybdenum and 2 cm thick acryl filters, from the film side. An ACR standard type 156 mammographic phantom was employed in evaluation of identifying capability. The X ray tube, phantom and screen-film combination were arranged with varying distances R1 and R2, as shown in Table 1, in which R1 was the distance between the focus point of the X ray tube and the phantom, and R2 was the distance between the phantom and the screen-film combination. Each of the exposed films was subjected to photographic processing at 34° C. for 90 sec., using automatic processor SRX-502 (available from Konica Corp.) with developer XD-SR and fixer XF-SR (both available from Konica Corp.). Images of the thus processed films were observed on a 10,000 lux viewing box. Five bodies of a plastic resin disc imitating tumor and five bodies of aluminum speck imitating micro-calcification were buried in the phantom, and the identifying capability was evaluated based on how many of them is identified by the naked eye. Identification capability of micro-calcification (A) and that of tumor (B) are shown in Table 1. In the Table, the value of "Identification Capability" indicated the number of the identified bodies. The value of "Overall Judgment" indicates the sum of the identification capability of A and B and the values of 6 or more are acceptable in practical use.

As shown in Table 1, the speed of photographic combination No. 1 was so low that the combination could not be separated from the position of the object to the extent capable of achieving the effect of refraction contrast (R2=0). In photographic combination No. 6, the speed was less than 200, so that the combination could also not be separated from the position of the object to the extent capable of achieving the effect of refraction contrast. As can be seen from photographic combination No. 7, when the speed exceeded 750, the X ray exposure amount decreased, resulting in an increase of X ray quantum mottling and leading to deteriorated graininess. In photographic combination No. 8, the sensitivity of the screen was less than 200 and the phosphor layer thickness was relatively small, so that absorption of X rays was decreased, resulting in increased x ray quantum mottles and leading to deteriorated graininess. In photographic combination No. 9, the screen sensitivity was more than 500 and the speed of the combination was so high that the X ray exposure amount, resulting in increased X ray quantum mottles and leading to deteriorated graininess. In photographic combination No. 10, the film sensitivity was less than 1.0, so that the combination could not be separated from the position of the object to a level capable of achieving the effect of refraction contrast. In photographic combination No. 11, the film sensitivity was more than 3.0 and the resulting higher speed of the combination reduced the exposure of X ray, resulting in increased X ray quantum mottles and leading to deteriorated graininess. In photographic combination No. 12, sharpness (CTF) was less than 0.5, resulting in deterioration in identifying capability. As shown in photographic combination No. 13, when the average particle size of the phosphor was less than 2 μm the sensitivity per phosphor amount (or phosphor layer thickness) was relatively low, and increasing the thickness to make the screen sensitivity more than 200 resulted in deteriorated sharpness. As shown in photographic combination No. 14, the phosphor having an average particle size of more than 7 μm resulted in increased scattering of phosphor luminescence, leading to deterioration in sharpness, even when the phosphor layer thickness was reduced. As shown in photographic combination No. 15, in a case of the phosphor layer exhibiting a filling factor of less than 60%, increased voids resulted in increased scattering of phosphor luminescence, leading to deterioration in sharpness, even when the phosphor layer thickness was reduced. As shown in photographic combination 16, when the binder content was less than 0.1% by weight, the phosphor layer was brittle. As exhibited in photographic combination No. 17, when the binder content was more than 5% by weight, the phosphor filling factor of the phosphor layer was reduced, resulting in increased light scattering in the phosphor layer and leading to deteriorated sharpness. Apparent in photographic combination Nos. 18 to 21 is that inclusion of the hydrophilic group increased the phosphor filling factor, leading to a screen exhibiting higher sensitivity and superior sharpness. Evidenced by photographic combination No. 22 is that the contrast of less than 2.5 led to deterioration in identifying capability. As shown in photographic combination No. 23, the contrast of more than 4.5 increased granularity, leading to deterioration in identifying capability.

2. The radiographic system of claim 1, wherein the radiographic system is a mammographic system.

3. The radiographic system of claim 2, wherein the object is a breast.

4. The radiographic system of claim 2, wherein the X ray source is a molybdenum tube.

5. The radiographic system of claim 1, wherein a distance between the X ray source and the object is not less than 50 cm, a distance between the X ray source and the photographic combination being not less than 75 cm.

6. The radiographic system of claim 5, wherein the X ray source is a molybdenum tube.

7. The radiographic system of claim 1, wherein the radiographic intensifying screen exhibits a sensitivity of 200 to 500.

8. The radiographic system of claim 1, wherein the speed of the photographic combination is a system speed based on a photographic speed of the light sensitive layer and a sensitivity of the radiographic intensifying screen.

9. A photographic combination for use in radiography to project a refraction contrast image comprising a radiographic intensifying screen and a silver halide light sensitive photographic material, wherein the photographic material comprises a support having on only one side of the support a light sensitive layer, the photographic combination exhibiting a speed of 200 to 750.

TABLE 1

| Combination No. | Screen | Film | $S_1$ | $S_2$ | $S_3$ | R1/R2 (m) | Sharpness (CTF) | Phosphor Size (μm) | Phosphor Filling Factor (%) | Binder (%) | Hydrophilic Group | Contrast | Identifying Capability A | Identifying Capability B | Overall Judgement | Remark |
|---|---|---|---|---|---|---|---|---|---|---|---|---|---|---|---|---|
| 1 | MD100 | CMH | 100 | 1 | 100 | 0.6/0 | 0.9 | — | — | — | — | 3.2 | 2 | 2 | 4 | Comp. |
| 2 | A | CMH | 250 | 1 | 250 | 0.5/0.25 | 0.82 | 3.1 | 62 | 1.5 | — | 3.2 | 4 | 4 | 8 | Inv. |
| 3 | A | a | 250 | 1.5 | 375 | 0.6/0.3 | 0.82 | 3.1 | 62 | 1.5 | — | 3.3 | 4 | 4 | 8 | Inv. |
| 4 | B | CMH | 450 | 1 | 450 | 0.8/0.4 | 0.54 | 5.3 | 61 | 1.5 | — | 3.2 | 5 | 4 | 9 | Inv. |
| 5 | B | b | 450 | 1.5 | 675 | 1.0/0.5 | 0.54 | 5.3 | 61 | 1.5 | — | 3.3 | 5 | 4 | 9 | Inv. |
| 6 | C | CMH | 180 | 1 | 180 | 0.6/0 | 0.95 | 3.1 | 62 | 1.5 | — | 3.2 | 2 | 2 | 4 | Comp. |
| 7 | D | c | 400 | 2 | 800 | 1.2/0.6 | 0.6 | 5.3 | 61 | 1.5 | — | 3.3 | 3 | 1 | 4 | Comp. |
| 8 | C | a | 180 | 2.5 | 450 | 0.8/0.4 | 0.95 | 3.1 | 62 | 1.5 | — | 3.3 | 4 | 2 | 6 | Inv. |
| 9 | E | CMH | 550 | 1 | 550 | 0.9/0.45 | 0.41 | 5.3 | 61 | 1.5 | — | 3.2 | 3 | 3 | 6 | Inv. |
| 10 | D | d | 400 | 0.8 | 320 | 0.5/0.25 | 0.6 | 5.3 | 61 | 1.5 | — | 3.3 | 2 | 4 | 6 | Inv. |
| 11 | F | e | 220 | 3.3 | 726 | 1.0/0.5 | 0.9 | 3.1 | 62 | 1.5 | — | 3.3 | 4 | 2 | 6 | Inv. |
| 12 | G | CMH | 480 | 1 | 480 | 0.8/0.4 | 0.46 | 5.3 | 61 | 1.5 | — | 3.2 | 2 | 4 | 6 | Inv. |
| 13 | H | CMH | 220 | 1 | 220 | 0.5/0.25 | 0.46 | 1.5 | 61 | 1.5 | — | 3.2 | 2 | 4 | 6 | Inv. |
| 14 | I | CMH | 220 | 1 | 220 | 0.5/0.25 | 0.46 | 10 | 55 | 1.5 | — | 3.2 | 2 | 4 | 6 | Inv. |
| 15 | J | CMH | 220 | 1 | 220 | 0.5/0.25 | 0.46 | 3.1 | 55 | 1.5 | — | 3.2 | 2 | 4 | 6 | Inv. |
| 16 | K | CMH | 220 | 1 | 220 | 0.5/0.25 | 0.9 | 3.1 | 62 | 0.08 | — | 3.2 | 4 | 3 | 7 | Inv. |
| 17 | L | CMH | 220 | 1 | 220 | 0.5/0.25 | 0.46 | 3.1 | 55 | 5.5 | — | 3.2 | 2 | 4 | 6 | Inv. |
| 18 | M | CMH | 250 | 1 | 250 | 0.5/0.25 | 0.94 | 3.1 | 65 | 1.5 | Yes | 3.2 | 5 | 5 | 10 | Inv. |
| 19 | M | f | 250 | 2 | 500 | 0.8/0.4 | 0.94 | 3.1 | 65 | 1.5 | Yes | 3.3 | 4 | 5 | 9 | Inv. |
| 20 | N | CMH | 450 | 1 | 450 | 0.8/0.4 | 0.68 | 5.3 | 66 | 1.5 | Yes | 3.3 | 5 | 5 | 10 | Inv. |
| 21 | N | f | 450 | 1.5 | 675 | 1.0/0.5 | 0.68 | 5.3 | 66 | 1.5 | Yes | 3.3 | 4 | 5 | 9 | Inv. |
| 22 | A | g | 250 | 1.5 | 375 | 0.6/0.3 | 0.82 | 3.1 | 62 | 1.5 | — | 2.3 | 3 | 4 | 7 | Inv. |
| 23 | A | h | 250 | 1.5 | 375 | 0.6/0.3 | 0.82 | 3.1 | 62 | 1.5 | — | 4.8 | 4 | 2 | 6 | Inv. |

What is claimed is:

1. A radiographing system comprising a X ray source and a photographic combination onto which an image of X rays emitted from the X ray source and passing through an object is projected and which comprises a radiographic intensifying screen and a silver halide light sensitive photographic material comprising a support having on only one side of the support a light sensitive layer, wherein the X ray image is one which has been edge-enhanced through refraction contrast enhancement and enlarged, the photographic combination exhibiting a speed of 200 to 750.

10. The photographic combination of claim 9, wherein the photographic combination is used for mammography.

11. The photographic combination of claim 9, wherein the screen exhibits a sensitivity of 200 to 500.

12. The photographic combination of claim 11, wherein the radiographic intensifying screen exhibits a contrast transfer function of 0.5 to 1.0 at a spatial frequency of 2 line/mm.

13. The photographic combination of claim 9, wherein the radiographic intensifying screen comprises a binder containing a hydrophilic group.

14. The photographic combination of claim 9, wherein the photographic material exhibits a sensitivity of 1.0 to 3.0 and an average contrast of 2.5 to 4.5.

15. A radiographing method, wherein an refraction contrast radiographic image is photographed using a photographic combination as claimed in claim 9 and wherein an X ray source, an object and the photographic combination are arranged in this order so that the distance between the X ray source and the object is not less than 50 cm and the distance between the object and the photographic combination is not more than 75 cm.

16. The radiographic method of claim 15, wherein the X ray source is a molybdenum tube.

* * * * *